United States Patent [19]
Matthews et al.

[11] Patent Number: 6,022,509
[45] Date of Patent: Feb. 8, 2000

[54] PRECISION POWDER INJECTION MOLDED IMPLANT WITH PREFERENTIALLY LEACHED TEXTURE SURFACE AND METHOD OF MANUFACTURE

[75] Inventors: Frank D. Matthews, Walpole; Salvatore Caldarise, Hanson, both of Mass.

[73] Assignee: Johnson & Johnson Professional, Inc., Rayham, Mass.

[21] Appl. No.: 09/157,004

[22] Filed: Sep. 18, 1998

[51] Int. Cl.⁷ .......................................................... B22F 3/12
[52] U.S. Cl. ................... 419/38; 419/2; 419/36; 264/44; 264/669
[58] Field of Search .................. 419/35, 36, 37, 419/38, 2; 264/44, 478, 669

[56] References Cited

U.S. PATENT DOCUMENTS

| | | | |
|---|---|---|---|
| 4,431,449 | 2/1984 | Dillon et al. | 75/246 |
| 4,964,907 | 10/1990 | Kiyota et al. | 75/235 |
| 5,336,465 | 8/1994 | Matsumaga et al. | 419/2 |
| 5,421,853 | 6/1995 | Chen et al. | 75/252 |
| 5,531,958 | 7/1996 | Krueger | 419/44 |
| 5,627,258 | 5/1997 | Takayama et al. | 528/338 |
| 5,639,402 | 6/1997 | Barlow et al. | 264/6 |
| 5,641,920 | 6/1997 | Hens et al. | 75/228 |
| 5,773,099 | 6/1998 | Tanaka et al. | 427/529 |
| 5,848,350 | 12/1998 | Bulger | 419/36 |

*Primary Examiner*—Ngoclan Mai
*Attorney, Agent, or Firm*—Nutter, McClennen & Fish, LLP

[57] ABSTRACT

An implant component adapted for bone attachment or replacement is molded from a feed stock which contains a soluble major binder, a backbone binder and structural powder material. After the feed stock is injection molded to form a compact or preform, the major binder is removed from the green article, leaving a structure of interconnected porosity or texture, while the backbone binder remains until the component is sintered. Preferably, the amount of the soluble binder is set to increase the porosity, or reduce the stiffness, of the finished component, thus introducing a biocompatible or growth-enhancing level of porosity or stiffness during the molding process. In further or alternative embodiments, the component may be injection molded onto or about a solvent-leachable spacer preform and/or adjacent to another injected or molded portion of the component which serves as a structural body, frame or shell. In these cases, all or a part of the molded portion may be formed with a conventional precision powder molding feed stock to achieve a high packing density/low shrinkage frame or support for the spacer preform or additional porous molding. The invention also includes constructions wherein the component body is injection molded against or about a support core or plate to form a hybrid article. The resulting implant component is unitized by the sintering process into a single article having the desired dimensions, strength and porosity.

9 Claims, 3 Drawing Sheets

PRECISION POWDER INJECTION MOLDED IMPLANT WITH PREFERENTIALLY LEACHED TEXTURE SURFACE AND METHOD OF MANUFACTURE

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention relates to implantable prostheses, such as structures or shaped articles to repair or replace bones, joints or hard skeletal parts. Articles of this type have traditionally been fabricated from strong or durable and biocompatible materials, using one or more manufacturing processes such as casting, forging, machining, coating and other industrial steps to form, shape and finish the article.

Precision powder injection molding (PPIM) is a recent refinement of metal injection molding (MIM) technology, a process that allows wet shaping of materials ranging from low carbon steels to intermetallic compounds, including traditional ceramics, high temperature ceramics, and refractory metals. The PPIM manufacturing technique is applicable to a wide variety of materials and uses, and has been applied to or is applicable to a large spectrum of specific manufacturing tasks, including the manufacture of tools, microelectronic packages, mechanical components of firearms, automotive components, and biomedical instruments. This technology has the potential to take MIM into a new era in terms of low manufacturing cost, achievable tolerances and component sizes, part-to-part consistency, and environmental friendliness. Presently, the process involves compounding the solid powder or powders which are the basic constituents of the finished part with a fluid or plastic carrier that enables the powdered material to flow for injection molding, and to maintain a stable shape when molded so that the intermediate part or compact can undergo further processing. The injection molding feed stock generally contains water soluble binder materials which are later dissolved out, and other, plasticized thermoset binder materials which remain, thus allowing the component to retain its shape until final sintering. These binder materials may also be selected to alter surface properties of constituent metal powders or to affect their chemistry, in addition to enhancing the flow of feed stock, the ultimate packing density of the solids and the dimensional stability of the molded green part. The powder constituents themselves may be selected with size, shape or elemental composition in a manner to increase solids density, improve alloying temperature, or otherwise improve characteristics such as strength, precision and ease of manufacture.

In the field of medical prostheses, porous coatings have previously been used on implants to improve cement fixation, and/or to provide a texture adapted for the ingrowth of new bone, so as to enhance the long-term fixation of the implanted device in position. Conventional approaches to creating and attaching a porous coating often involve locally attaching small features such as beads or powders, by techniques such as sintering, flame spraying, co-casting or welding; or they involve creating a porous region of the device by techniques such as etching or machining, or attaching a separate previously textured plate.

Cost is a major concern in the creation of such surgical components, and additional process steps such as sintering of a porous coating onto an implantable prosthesis add time and production costs to the product delivery. High temperature sintering can also degrade physical properties of the material which forms the body of the prosthesis. Moreover, the design of ingrowth geometries is limited by the powder particles utilized. Ceramic composites made by this approach use relatively large, e.g., 10–50 micron, agglomerates of polymer-coated inorganic particles. These agglomerate powders may spread into uniform layers and fuse to yield porous green parts that have relative densities near 50%, thus providing deep or internal connective passages, and having sufficient strength to be handled and shipped. This ability to create a structure of interconnected pores in a bioceramic body may be used for fostering bone growth, or for implementing hybrid constructions such as metal matrix/ceramic bodies which combine the wear propertied ceramic with the strength or toughness of metal for prosthetic implants, such as artificial hips. However, these hybrid porous structures can be difficult to manufacture.

In prior art PPIM systems, powders and binders are mixed to form the feed stock which is to be powder injection molded. The feed stock production is the most important step in the powder injection molding technology, and if components are manufactured from inferior feed stock, it will be difficult, if not impossible, to produce consistent components of high tolerance without resorting to secondary or further processes such as coining or machining. Thus, feed stock homogeneity and compositional accuracy are a major challenge for manufacturers using powder injection molding. Problems with components such as cracking and non-uniform shrinkage which arise during de-binding and sintering can often be traced to faulty feed stock formulation. However, the compounding of a feedstock is generally directed to these two major problems, which are addressed, for example by generally employing relatively small amounts of binder so that the molded article has a high density of solids, or is addressed by employing carrier portions that allow the use of smaller solid particles, thus increasing both the local uniformity and the packing density of the green article.

Conventional practice in powder injection molding is that powders having the elemental composition of the desired final product are mixed with a binder mixture and possibly various conditioners or additives to form the feedstock. The binder may be a heterogeneous mixture containing two primary components. The first component of the binder, also referred to as the major component, is typically a polymer component such as a wax or a water soluble polymer material, that provides, in part, a flowable, plastic or lubricating medium to facilitate the transport of the powder into the mold. The major component is also typically selected to provide good moldability and to be easily removed during the de-binding phase. Some suitable binder components of this type may be polymers of acrylic or methacrylic acid, acrylamide, vinyl acetate, ethylene glycol and various block polymers or copolymers. The second component of the binder, also referred to as the backbone component, is generally added in a lesser amount to provide strength or adhesion of the solids, i.e., to assure that the molded compact retains its shape after molding, while the first component is being removed and until the molded part is sintered. The backbone component may, for example, be a plasticized thermosetting organic material. This material may be removed later, just before the powder particles start to sinter, for example by baking out, by pyrolysis or catalytic breakdown, by chemically reactive removal or even by combination with the powder constituents near the sintering temperature. The result is a strong molded component, which sinters to form a finished part of precise dimension and improved strength. Further specific aspects of powder injection molding as well as suitable binder materials for feed stock formulation and other materials for coating of feed stock powders or enhancing binder behavior during the mixing, injection, mold separation or debinding procedures, are discussed in the following U.S. Patents and the texts referred to therein: U.S. Pat. Nos. 5,691,920; 5,639,402; 5,627,258; 5,531,958; and 5,421,853.

However, to applicant's knowledge, components made by precision powder injection molding are generally solid bodies of relatively dense material. The creation of texture in such a body would appear to require the use of a texture-patterned mold surface in the original molding step. The provision of such a pattern on the mold surface might prevent removal of the molded article from the mold, and even if this approach were found to be feasible, it would be useful for only a limited range of texture dimensions and shapes. Another approach to texturizing could perhaps be implemented by steps of separately attaching to or machining a texture region on an article molded by PPIM, although this would result in a more costly manufacturing process.

BRIEF SUMMARY OF THE INVENTION

The present invention addresses the limitations of the prior art by providing a prosthetic or implantable device component and a method of making the component, wherein a desired surface texture or pore structure is created in an implant body by forming the body as an injection molded powder compact having a soluble component distributed in communicating meanders between powder particles, removing the soluble component, and sintering the molded compact. Preferably, the soluble component is a major binder component which enhances powder flow for molding, and this component is present in a sufficiently large quantity to achieve a biologically conducive porosity in the article so formed by the solids/powder component. A lesser quantity of backbone binder is added to the feed stock, and provides strength in the molded compact, remaining until sintering. In another embodiment, the soluble component initially is introduced as a solid component in the form of a sacrificial spacer preform, such as a screen or grid, which is made of a soluble material, such as a soluble hydrophilic polymer material. In that case, the body is injected molded onto or about the spacer preform, so that when the spacer is dissolved from the molded part it leaves a network of intercommunicating pores or passages at the surface of the body. The soluble components or removable binder components of the feed stock in accordance with this aspect of the invention may constitute from several percent to fifty per cent or more of the feed stock, and one or more large grain powders or solids may further be employed to achieve a loose packing density that assures or further enhances the open structure or porosity of the molded compact. By employing high levels of binder, optionally with coarse, granular or poorly-packable powders, an open pore or coarse texture compact is molded.

After molding, the compact is treated to remove the first binder component, to remove the second binder component, and to sinter it. Upon sintering, the dimensions of the pore structure of the compact shrink, creating finer pore structures. The construction also lends itself to the creation of implant articles with a modulus or bending stiffness modified by a reduced solids density. The invention also contemplates the fabrication of prostheses wherein a first portion of the prosthesis is formed of a high solids density feed stock, and a second portion is formed of a porous, texture-forming or lower solids density feed stock.

BRIEF DESCRIPTION OF THE DRAWINGS

The foregoing features of this invention, as well as the invention itself, may be more fully understood from the following description and illustrative drawings, in which.

DETAILED DESCRIPTION OF THE INVENTION

The invention will be best understood after a brief discussion of current precision metal powder injection molding technology, which the present invention modifies in part and applies to a generally different class of structures to form structured implants. By the term "structured", applicant refers to a characteristic porous or open structure, when viewed at a macroscopic level, of the finished material constituting an article molded by the processes of the present invention, as will be described further below.

The use of metal and other powders to form objects by first compacting the powders in a mold to form a preform, then sintering the preform to consolidate and strengthen it is well established. That technology has a number of advantageous features; for example it is often possible to arrange that the beginning powder ingredient has a more desirable physical property, such as hardness or crystal structure, than would be achievable if one were to employ alternative casting, machining or forging methods for fabricating the final object from a bulk solid or liquid material. However, until relatively recently, the manufacture of sinterable powder objects was done by casting or press forming, rather than injection molding the powders, since the powders may typically flow too poorly to be suitable for injection, and lack sufficient strength, even after compaction, to undergo the handling necessary for subsequent processing steps, such as demolding and sintering. As noted above, current precision powder injection molding technology has generally addressed this limitation by providing binder ingredients that plasticize and strengthen the feed stock material, so that it flows and may be injection molded, and so that the molded product has sufficient strength for handling when still green. These carrier or binder ingredients, as noted above, may include a soluble major component and a backbone or strengthening component as will be familiar to those skilled in the field. Further, by lubricating or increasing the flowability of the feedstock, powder densities approaching 100% may be attained, greatly reducing the amount of shrinkage when the article is sintered. Smaller particles may also be employed, improving both the solids density and the uniformity of composition or the alloying which may occur upon sintering. Preferably the major binder or carrier component is water soluble, so the molding technology has very little environmental impact.

Figure 1A:
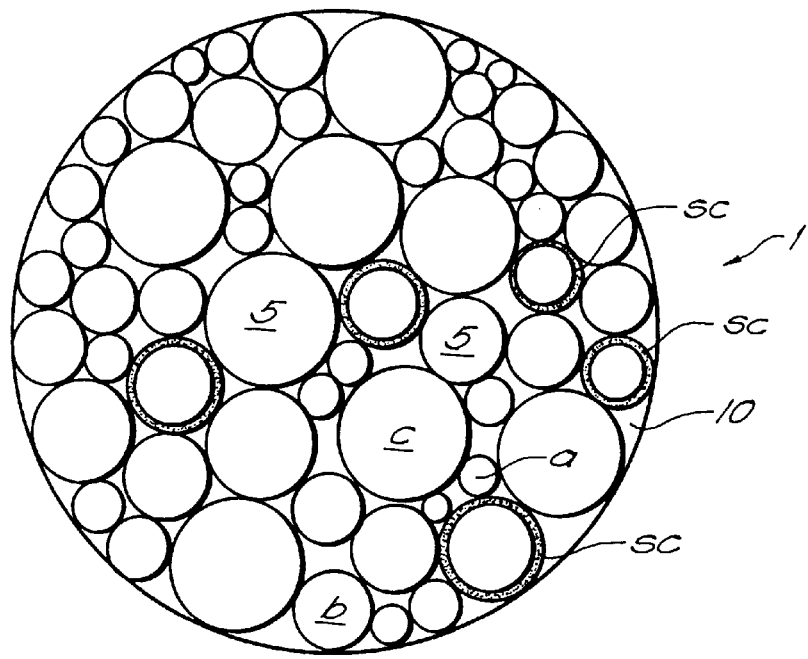
FIG. 1A is a conceptual cross-sectional view illustrating a prior art precision powder injection molding feed stock.

FIG. 1A illustrates a cross sectional view through a small and representative region of a prior art PPIM feed stock 1, which is assumed to be homogeneous. As shown, the general composition includes particles 5 of one or more general sizes, denoted a, b, c which may also be of different elemental or chemical composition. For example the particles may include relatively large grains of a steel component to provide hardness or wear strength, and smaller particles of a glass or alloying component to improve toughness or reduce the required sintering temperature. The particles may also be all of the same material, with different sizes employed to increase the solids packing density of the molded article rather than to affect its metallurgical or other properties. The injection molding is carried out under pressure, so the small amount of interstitial space between particles is entirely filled with the carrier or binder 10, which, as discussed above includes a fluid or plastic carrier substance and a generally lesser quantity of a backbone or strengthener substance, possibly with other substances, which in this Figure are indicated schematically as a thin surface coating sc on at least some of the powder particles. Illustratively, the binder 10 occupies a relatively small or lesser portion of the feed stock than does the powder, and may occupy well under ten percent of the cross-sectional area as viewed in a representative section. As a result, the powders achieve good particle-to particle contact, and the removal of binder and sintering of the molded compact results in a height solids injection molded article with only minor empty space being present in its interior, and a surface roughness which may, for example, be considerably below the dimension of the largest grains of powder present in the feed stock.

In accordance with a principal aspect of the present invent, applicant forms an implant component from an injection molding feed stock wherein the feed stock is compounded of solid powders and a soluble binder to impart a porosity of interconnected passages to the solid article molded therefrom. In general the soluble binder forms a substantial component of the feed stock, and is removed prior to sintering to leave a compact article of sponge or open-pored material. While in one aspect, discussed further below, this is done with a soluble spacer and may utilize a conventional high density feed stock, applicant preferably employs a specially formulated feed stock to achieve such structural porosity.

Figure 1B:
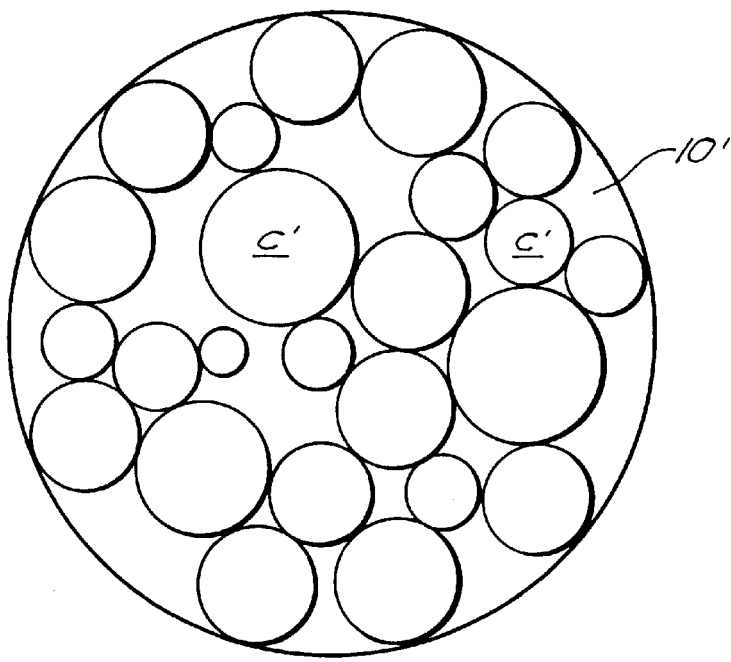
FIG. 1B is a corresponding view of a feed stock of the present invention for forming a textured implant component.

FIG. 1B illustrates schematically a feed stock according to this aspect of the present invention for forming prosthetic implants. As shown therein, the feed stock has a generally uniform composition including a binder 10' and solid particles c' wherein the binder 10' constitutes a generally larger than conventional proportion, between about ten to about fifty percent or more, of the cross-sectional area of the feed stock mix, and, when molded, communicates in continuous strands or masses about and between the powder particles. This may be achieved, for example, by providing correspondingly high proportions of binder in the feedstock, or, equivalently, reduced levels of powder. The porosity may be further enhanced by employing, as one or more component powders in the feed stock, powders having a particle size and/or shape which packs poorly.

Thus, in accordance with a principal feature of this aspect of the invention, a controlled amount and distribution of void space is created in a molded sintered product tailored for cement enhancement and/or biological ingrowth, and/or reduced structural stiffness. In each embodiment a controlled pattern of molding porosity is created by the feed stock composition. In particular embodiments the ingrowth surface geometry may also be implemented by incorporating additional mold forms or spacer elements. In each case, by forming the component geometry or principal body and the intrinsic texture of at least a portion of the body in a single molding, a complicated geometry with a desired surface or through-body depth texture is created in a cost-effective manner. In further embodiments two or more layers of feed material may be employed, to form prosthetic articles in which the pore structure and/or the porosity is graded or discretely changing with depth or location.

While the discussion below assumes a general knowledge of PPIM technology, in directing the molding process to the creation of a porous or structurally more open compact, applicant contemplates several new approaches to feed stock formulation. As a first matter, the feed stock of applicant's process is preferably compounded to have the major, or soluble binder component present in intercommunicating or attached regions. Viewed from the complementary perspective of powder packing, this requires that the solids contact to an extent that leaves interconnected spaces between particles filled with binder. This is achieved in one embodiment of the invention by compounding the feed stock with powders having shapes and sizes that result in poor packing, so that relatively large spaces exist between particles to form pores or passages. Depending on the intrinsic flow properties of the powders, this may be done without substantially changing the level of major binder component. It may also be achieved in a basic embodiment by compounding the feed stock with a lower percentage of powder, or a lower powder/binder ratio, than the level which the theoretical packing density of the powder indicates is required to fill the space or achieve maximal solids density in the feed stock. This causes a substantial portion of the cross section to be occupied by the soluble binder. These various approaches may be briefly characterized as a "coarse or shaped solids" feed stock formulation, and a "sparse solids or fat binder" feed stock formulation. Various refinements of the first formulation may, for example, mix different size or shape powders to assure inefficient packing, such as mixing large cubic grains with smaller spherical powders, or mixing flake-shaped and grain-shaped powders, to assure a poor level of interfitting of the solids. Applicant also contemplates assuring the presence of binder-filled spaces by employing a very viscous binder, by applying specialized coatings to the powder ingredients which result in additional open space when baked out, or by using a two phase binder or an emulsion-like fluid in the binder component. In the latter formulation, droplets of or material in one phase in the binder may form a nonremoved residue which serves, for example, as a catalyst, alloy or flux component during sintering.

Figure 2:
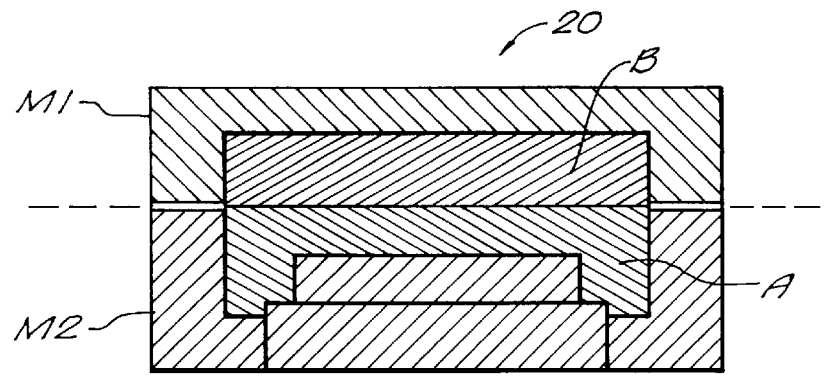
FIG. 2 is a schematic view in section illustrating one method of the present invention for forming an injection molded texture implant component.

FIG. 2 schematically illustrates both the molding process and the form of a manufactured prosthetic component in a first embodiment of the invention. The Figure illustratively shows a cross sectional view of the article 20 within the injection mold. The mold is shown for the sake of illustration as having first and second mold body parts M1, M2 which seal together in a well known manner to define a cavity shown centrally therebetween. The cavity is filled with an injection feed stock in separate times or operations to form a first partial component denoted A, topped by a second partial component labeled B. The component A may be formed from the feed stock of FIG. 1A, so that it is a fully dense, non-shrinkable precision molded part. The partial component B, on the other hand, is formed from a feed stock as shown in FIG. 1B, to result in that portion of the completed molding A+B having an open structure when sintered in the preferentially located areas. The illustrated prosthesis component is a raised plate, which thus enjoys the property of having an as-formed precision lower fitting surface, and a porous upper portion, both of which are molded together and are then sintered in a single operation resulting in a simple manufacturing process and little generation of thermal strain. The binder systems employed for the A and B portions may be fully compatible with each other, or even differ solely in their proportions of components. Further, the mold may be constructed with various springloaded, retractable or selectively inserted spacer portions which are positioned or operated during initial operation, for example, to temporarily fill or block the space within the mold that is later to constitute the mold cavity for adding the pore-forming "B" material. This allows the first part to be precision molded and remain in the mold body during continuing injection of the second part, so the two parts are formed in the same mold in an automated sequence.

Figure 3A:
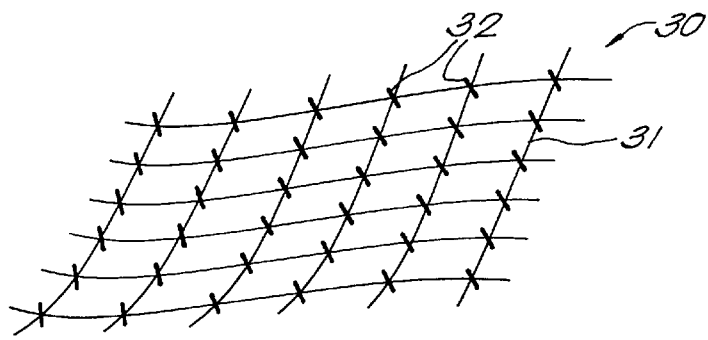
FIGS. 3 and 3A are schematic cross-sectional views illustrating another method of the present invention for forming an injection molded texture implant component.
Figure 3:
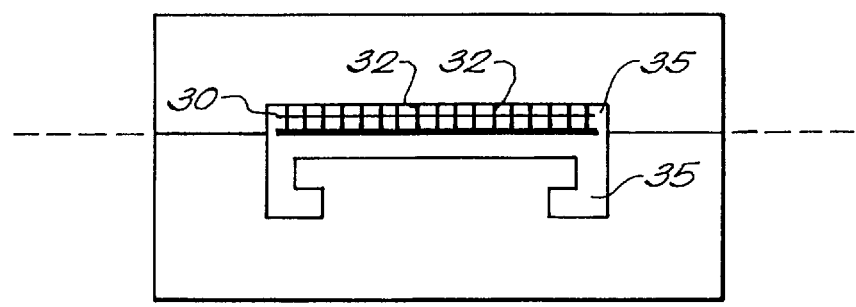

FIGS. 3 and 3A illustrate a method and component in accordance with a second embodiment of the invention. In accordance with this embodiment, the powder feed stock utilized for forming the component is preferably a fully optimized precision molding feed stock, so that it is dense, strong and dimensionally stable. However, the feed stock is molded around a spacer preform 30, shown in FIG. 3A, which has been manufactured in a shape to impart the intended porosity. The spacer preform is formed of a water-soluble or otherwise removable polymer material, which may be the same material or the same class of material as the first feed stock binder component. After the article is molded against the spacer, the article is removed from the mold and the spacer is removed from the molded article at the same time as, or in a similar manner to the debinding of the article itself. Thus, the open structure in the molded article is created simply as the cavity, invaginations or porosity left by removal of the spacer preform from the green article. As illustrated in FIG. 3A, the spacer preform may have a shape similar to a screen or lattice 31 with additional out of plane projections 32. Such preform is readily made, for example by press molding in a waffle-shaped press, by stamping from a sheet, by a hybrid process of weaving the screen and adding plastic projections, or by any other suitable forming process. Then as shown in FIG. 3, the spacer preform is placed within a mold cavity adjacent a surface of the mold, and the texture prosthesis body 35 is injection molded about it. The projections 32 thus extend to the outer surface of the molded article, and when removed in the debinding process, leave empty passages which provide entry pores at that surface, illustratively the top, of the molded article. The entry pores lead into the lattice of interconnected passages remaining after removal of the interconnected crossing strands 31 which constituted the screen 30 lying just below the surface or the molded article. This provides a regular array of texture passages having a controlled size and spacing, which may thus be optimized for new bone growth.

It will be understood further that with the advances in binder formulations now available for PPIM processes, the binder material may be removed quickly and efficiently even from fairly thick molded components. Therefore, when the present process is not being employed to provide a region for surface ingrowth of bone, the spacer preform need not be positioned immediately adjacent to the surface in order for it to be effectively removed. Instead, it may be positioned deeper within the molded body, to create an internal region of decreased stiffness or increased flexibility. Furthermore several such spacers may be provided in different regions and/or to achieve several different effects in a single component, such as in a stem component, so as to achieve both surface growth compatibility for bone attachment and structural compliance for optimization of mechanical properties.

Figure 4:
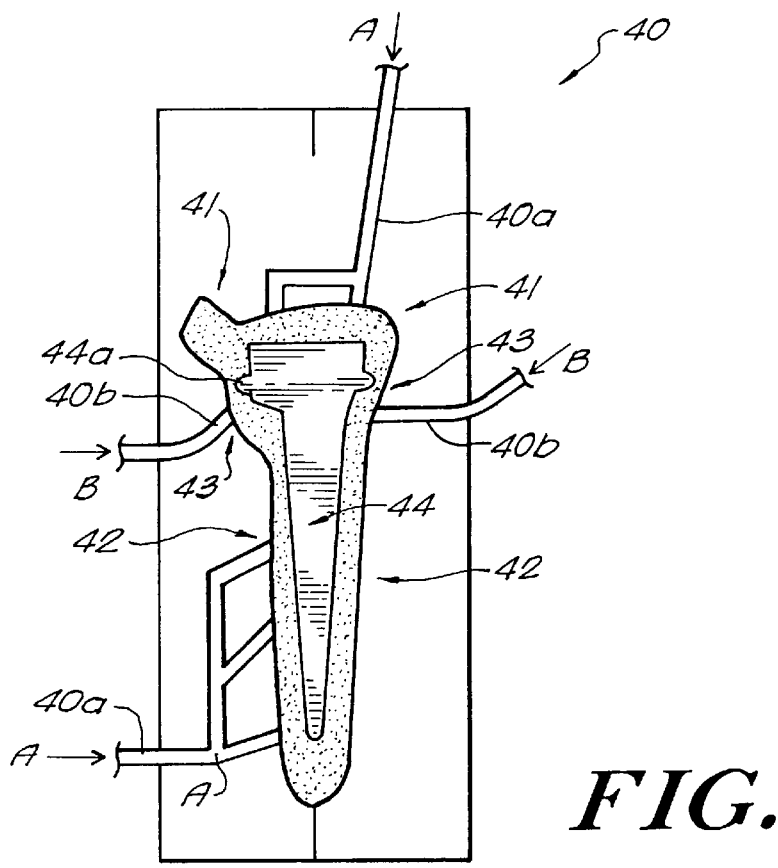
FIG. 4 is a schematic cross-sectional view illustrating another method of the present invention for forming an injection molded texture implant component.

FIG. 4 shows yet another embodiment 40 of the invention. In this embodiment, the injection mold is set up with a first plurality of feed stock inlet passages 40*a* for injecting the PPIM "A" feedstock into the mold cavity, and a second plurality of inlet passages 40*b* for the "B" feed stock. The resulting molded article possesses a leachable porosity or texture region 43 in the vicinity of the inlets 40*b*, with a uniform and thermally compatible surrounding precisely-dimensioned remainder composed of the less porous or effectively solid material filled by inlets 40*a*. This embodiment may also be implemented by injection molding about a core body comprised of a previously made, non-precision casting 44, such as a support column or plate which fits within the stem or plate injection mold. The precision full strength solid molded surface regions 41,42 and porous or texture regions 43 are both formed on the body 44. The internal support body 44 may have a shape that operates during injection molding to restrict the flow of one or both feed stocks, by a feature such as the circumferential ridge 44*a*, to assure that the leachable texture feed stock fills an identified region on the component surface, such as the neck of a femoral component, or does not extend greatly into a region of the prosthesis required to have smoother finish or stiffer matrix strength.

Figure 5:
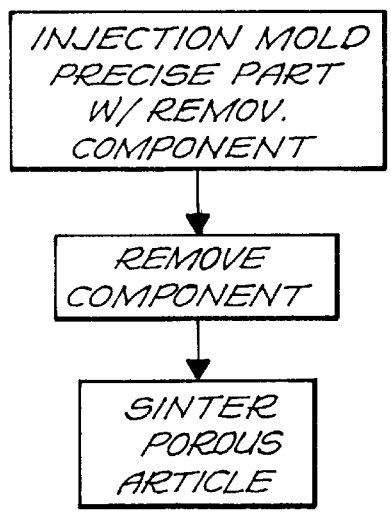
FIG. 5 is a chart showing steps of a method in accordance with the present invention.

Thus, in general, it will be seen that the method of the present invention is applicable to a range of constructions, such as stems, plates and entire prostheses, and offers the potential for a single operation which provides both a high degree of dimensional precision and an open or porous material structure. As shown in FIG. 5, the method steps involve simply injection molding with an excess of removable binder or a spacer component that is removed compatibly with the binder, and then leaching and subsequently sintering the injected compact to form a substantially finished porous article.

Having described several illustrative embodiments of the invention, other embodiments incorporating the inventive concepts and improvements will occur to one of ordinary skill in the art. Therefore the invention is not to be limited to disclosed embodiments but rather should be limited only by the spirit and scope of the invention as set forth herein and in the claims appended hereto, and their equivalents read and understood in light of the knowledge common in the art.

What is claimed is:

1. A method of forming a prosthetic implant or part thereof, such method comprising the steps of preparing a feedstock comprising at least a major binder, a backbone binder and a structural powder, and molding the feedstock to form a molded implant component wherein the major binder is a solvent-removable binder, and the step of preparing the feedstock includes preparing the feed stock with said major binder present in an amount effective, upon removal of said major binder, to introduce a biological level of porosity or bending stiffness in the molded implant component, such that molding of the implant component simultaneously shapes said implant component and introduces said biological level.

2. The method of claim 1, wherein the step of molding the feedstock includes selectively applying the feedstock in a position to form a porous portion of the implant component.

3. The method of claim 1, wherein the step of molding the feedstock includes the step of molding the feedstock onto a preformed and solvent-leachable spacer component.

4. The method of claim 3, further comprising the step of removing said major binder and said solvent leachable spacer component.

5. The method of claim 4, further comprising the step of sintering the molded implant component, said step of sintering being performed after said step of removing.

6. The method of claim 1, further comprising the step of sintering the molded component, and wherein the step of molding is performed to form said molded implant component having a size substantially greater than a desired size of said component after sintering.

7. The method of claim 2, further comprising the step of sintering the molded component, and wherein the step of molding is performed to form said molded implant component of a size substantially greater than a desired size of said component after sintering.

8. The method of claim 1, wherein the step of molding the feedstock to form a molded implant component is performed by molding a portion of the implant with a PPIM feedstock having a solids packing density above about ninety percent to form a precision implant body part, and also molding a further portion of the implant adjacently with said precision implant body part to introduce said biological level.

9. A method of forming an implant or part thereof, such method comprising the steps of preparing a feedstock comprising at least a major binder, a backbone binder and a structural powder, and molding the feedstock to form a molded implant component having a biologically conducive porosity or stiffness wherein the major binder is a solvent-removable binder, and the step of molding the feedstock includes the step of molding the feedstock together with a solvent-removable spacer in a mold cavity to form a molded article incorporating the spacer such that removal of said spacer and major binder, and sintering the molded article introduce a biological level of porosity or bending stiffness in the molded implant component, whereby molding of the implant component simultaneously determines the shape and said biological level of the implant component.

* * * * *